(12) United States Patent
Oikawa (10) Patent No.: US 11,840,768 B2
(45) Date of Patent: Dec. 12, 2023

(54) CARBON DIOXIDE TREATMENT DEVICE AND METHOD OF PRODUCING CARBON COMPOUND

(71) Applicant: HONDA MOTOR CO., LTD., Tokyo (JP)

(72) Inventor: Hiroshi Oikawa, Wako (JP)

(73) Assignee: HONDA MOTOR CO., LTD., Tokyo (JP)

(*) Notice: Subject to any disclaimer, the term of this patent is extended or adjusted under 35 U.S.C. 154(b) by 0 days.

(21) Appl. No.: 17/680,418

(22) Filed: Feb. 25, 2022

(65) Prior Publication Data
US 2022/0290315 A1 Sep. 15, 2022

(30) Foreign Application Priority Data
Mar. 11, 2021 (JP) .................................. 2021-039199

(51) Int. Cl.
*C25B 3/25* (2021.01)
*C25B 3/26* (2021.01)
(Continued)

(52) U.S. Cl.
CPC .............. *C25B 3/26* (2021.01); *B01D 53/1425* (2013.01); *B01D 53/1475* (2013.01);
(Continued)

(58) Field of Classification Search
CPC ........... C25B 3/26; C25B 15/083; C25B 3/03; C25B 9/17; C01B 32/50; B01D 53/1425; B01D 53/1475
See application file for complete search history.

(56) References Cited

U.S. PATENT DOCUMENTS

| | | | |
|---|---|---|---|
| 2011/0237839 A1 | 9/2011 | Waldstein | |
| 2014/0151240 A1* | 6/2014 | Bedell | B01D 53/1475 205/462 |

(Continued)

FOREIGN PATENT DOCUMENTS

| | | |
|---|---|---|
| CN | 201799208 | 4/2011 |
| CN | 102240497 | 11/2011 |

(Continued)

OTHER PUBLICATIONS

Japanese Office Action for Japanese Patent Application No. 2021-039199 dated Aug. 2, 2022.
(Continued)

*Primary Examiner* — Zulmariam Mendez
(74) *Attorney, Agent, or Firm* — AMIN, TUROCY & WATSON, LLP (57) ABSTRACT

What is provided is a carbon dioxide treatment device having high energy efficiency for recovering and reducing carbon dioxide, and a method of producing a carbon compound using the carbon dioxide treatment device. In a carbon dioxide treatment device (100) including a recovery device (1) that recovers carbon dioxide, an electrochemical reaction device (2) that electrochemically reduces carbon dioxide recovered by the recovery device (1), and a homologation reaction device (4) that increases the number of carbons by multimerizing ethylene generated when carbon dioxide is reduced in the electrochemical reaction device (2), and in an absorption unit (12) of the recovery device (1), carbon dioxide gas is absorbed into an absorption liquid (A1), an absorption liquid (A2) that has absorbed carbon dioxide is heated in a discharge unit (13), and a carbon dioxide gas (G3) is discharged, and heat generated in a multimerization reaction in a homologation reaction device (Continued)

(4) is used to heat the absorption liquid (A2) in the discharge unit (13).

4 Claims, 3 Drawing Sheets

(51) Int. Cl.
  *B01D 53/14* (2006.01)
  *C25B 3/03* (2021.01)
  *C25B 9/17* (2021.01)
  *C01B 32/50* (2017.01)
  *C07C 2/06* (2006.01)
  *C07C 29/84* (2006.01)
  *C25B 15/08* (2006.01)

(52) U.S. Cl.
  CPC ............... *C01B 32/50* (2017.08); *C07C 2/06* (2013.01); *C07C 29/84* (2013.01); *C25B 3/03* (2021.01); *C25B 9/17* (2021.01); *C25B 15/083* (2021.01); *C01B 2210/0025* (2013.01)

(56) References Cited

U.S. PATENT DOCUMENTS

2018/0264429 A1* 9/2018 Sugano ................. B01J 19/245
2018/0265440 A1 9/2018 Kudo et al.

FOREIGN PATENT DOCUMENTS

| CN | 108570690 | 9/2018 |
| JP | 2008-536852 | 9/2008 |
| WO | 2018/232515 | 12/2018 |
| WO | 2020/109295 | 6/2020 |

OTHER PUBLICATIONS

Chinese Office Action for Chinese Patent Application No. 202210164384.5 dated Jul. 7, 2023.

* cited by examiner

CARBON DIOXIDE TREATMENT DEVICE AND METHOD OF PRODUCING CARBON COMPOUND

BACKGROUND OF THE INVENTION

Field of the Invention

The present invention relates to a carbon dioxide treatment device and a method of producing a carbon compound.

Description of Related Art

A technology for recovering carbon dioxide in an exhaust gas or air and electrochemically reducing it to obtain a valuable substance is a promising technology that can achieve carbon neutrality, but economic efficiency is the biggest issue therewith. In order to improve economic efficiency, it is important to improve energy efficiency in recovering and reducing carbon dioxide.

As the technology for recovering carbon dioxide, a technology in which carbon dioxide in a gas is physically or chemically adsorbed on a solid or liquid adsorbent, and then desorbed with energy such as heat is known. In addition, as the technology for electrochemically reducing carbon dioxide, a technology in which carbon dioxide gas is supplied from the side of a gas diffusion layer opposite to a catalyst layer to a cathode in which the catalyst layer is formed using a carbon dioxide reduction catalyst on the side of the gas diffusion layer in contact with an electrolytic solution and is electrochemically reduced is known (for example, Patent Document 1).

PATENT DOCUMENTS

[Patent Document 1] PCT International Publication No. WO 2018/232515

SUMMARY OF THE INVENTION

However, in the related art, a technology for recovering carbon dioxide and a technology for electrochemically reducing carbon dioxide haven been researched and developed separately. Therefore, although the overall energy efficiency when these technologies are combined can be determined in a multiplier manner from the efficiency of each technology, there is room for further improvement. Therefore, it can be said that it would be meaningful to improve the overall energy efficiency when these technologies are combined.

An object of the present invention is to provide a carbon dioxide treatment device having high energy efficiency for recovering and reducing carbon dioxide, and a method of producing a carbon compound using the carbon dioxide treatment device.

The present invention provides the following aspects.

(1) A carbon dioxide treatment device according to one aspect of the present invention (for example, a carbon dioxide treatment device 100 of an embodiment) includes a recovery device that recovers carbon dioxide (for example, a recovery device 1 of the embodiment), an electrochemical reaction device that electrochemically reduces carbon dioxide recovered by the recovery device (for example, an electrochemical reaction device 2 of the embodiment), and a homologation reaction device that increases the number of carbons by multimerizing ethylene generated when carbon dioxide is reduced in the electrochemical reaction device (for example, a homologation reaction device 4 of the embodiment), wherein the recovery device includes an absorption unit that brings carbon dioxide gas into contact with an absorption liquid and absorbs carbon dioxide into the absorption liquid (for example, an absorption unit 12 of the embodiment), and a discharge unit that heats the absorption liquid that has absorbed carbon dioxide and discharges carbon dioxide gas (for example, a discharge unit 13 of the embodiment), and wherein the discharge unit heats the absorption liquid using heat generated in a multimerization reaction of the homologation reaction device.

(2) A carbon dioxide treatment device according to one aspect of the present invention (for example, a carbon dioxide treatment device 200 according to an embodiment) includes a recovery device that recovers carbon dioxide, an electrochemical reaction device that electrochemically reduces carbon dioxide recovered by the recovery device, and an ethanol purifying device that purifies ethanol generated when carbon dioxide is reduced in the electrochemical reaction device, (for example, an ethanol purifying device 5 of the embodiment), wherein the recovery device includes an absorption unit that brings carbon dioxide gas into contact with an absorption liquid, and absorbs carbon dioxide into the absorption liquid, and a discharge unit that heats the absorption liquid that has absorbed carbon dioxide and discharges carbon dioxide gas, the ethanol purifying device includes a distillation column that separates ethanol contained in an electrolytic solution of the electrochemical reaction device (for example, a distillation column 51 of the embodiment), and a heat source device is shared by the discharge unit and the distillation column (for example, a heat source device 6 of the embodiment).

(3) The carbon dioxide treatment device according to one aspect of the present invention may further include a power storage device that supplies power to the electrochemical reaction device (for example, a power storage device 3 of an embodiment), wherein the power storage device may include a conversion unit that converts renewable energy into electrical energy (for example, a conversion unit 31 of the embodiment), and a storage unit that stores electrical energy converted by the conversion unit (for example, a storage unit 32 of the embodiment).

(4) A method of producing a carbon compound according to one aspect of the present invention is a method of producing a carbon compound using the carbon dioxide treatment device (1), including a process of recovering carbon dioxide, a process of electrochemically reducing the recovered carbon dioxide to obtain ethylene, and a process of multimerizing ethylene generated when carbon dioxide is reduced.

(5) A method of producing a carbon compound according to one aspect of the present invention is a method of producing a carbon compound using the carbon dioxide treatment device (2), including a process of recovering carbon dioxide, a process of electrochemically reducing the recovered carbon dioxide to obtain ethylene, and a process of purifying ethanol generated when carbon dioxide is reduced.

According to the aspects (1) to (5), it is possible to provide a carbon dioxide treatment device having high energy efficiency for recovering and reducing carbon dioxide, and a method of producing a carbon compound using the carbon dioxide treatment device.

DETAILED DESCRIPTION OF THE INVENTION

First Embodiment (Carbon Dioxide Treatment Device)

Figure 1:
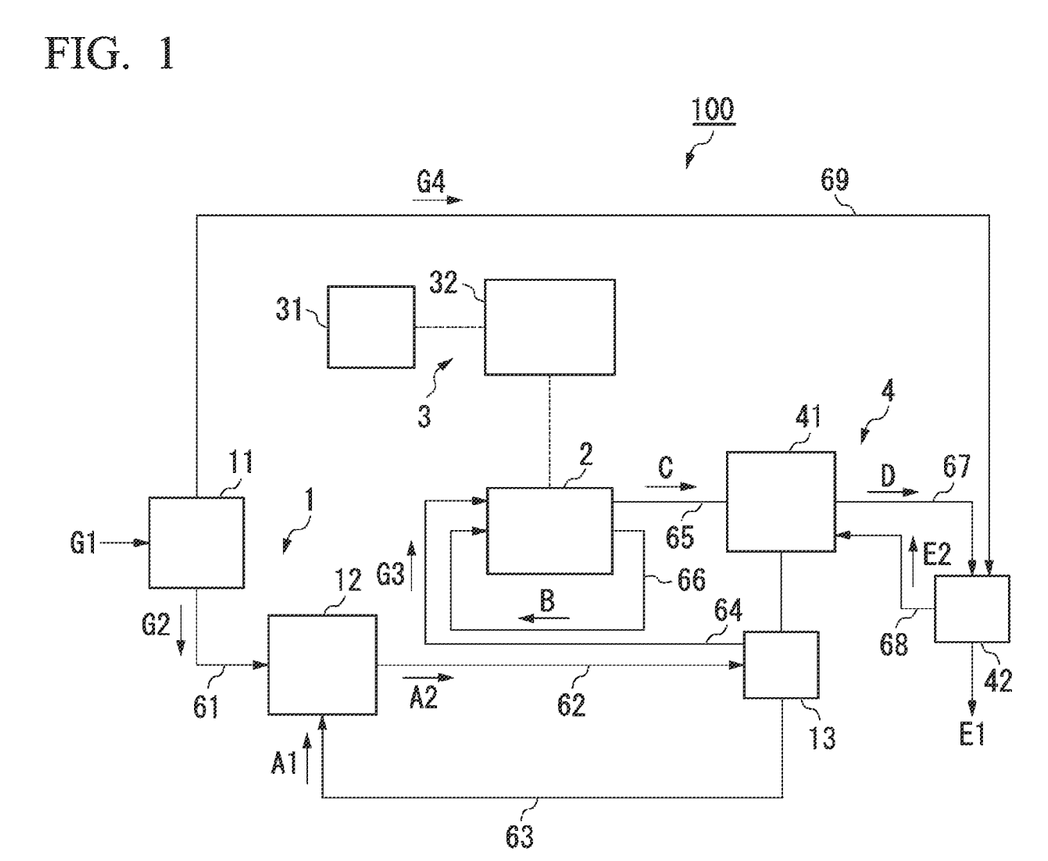
FIG. 1 is a block diagram showing a carbon dioxide treatment device of a first embodiment.

As shown in FIG. 1, a carbon dioxide treatment device 100 according to one aspect of the present invention includes a recovery device 1, an electrochemical reaction device 2, a power storage device 3, and a homologation reaction device 4. The recovery device 1 includes a concentration unit 11, an absorption unit 12, and a discharge unit 13. The power storage device 3 includes a conversion unit 31 and a storage unit 32 electrically connected to the conversion unit 31. The homologation reaction device 4 includes a reaction container 41 and a gas-liquid separator 42.

In the carbon dioxide treatment device 100, the concentration unit 11 and the absorption unit 12 are connected via a gas flow path 61. The absorption unit 12 and the discharge unit 13 are connected via a liquid flow path 62 and a liquid flow path 63. The discharge unit 13 and the electrochemical reaction device 2 are connected via a gas flow path 64. The electrochemical reaction device 2 and the reaction container 41 are connected via a gas flow path 65. The reaction container 41 and the gas-liquid separator 42 are connected via a gas flow path 67 and a gas flow path 68. The concentration unit 11 and the gas-liquid separator 42 are connected via a gas flow path 69.

These flow paths are not particularly limited, and known pipes and the like can be appropriately used. In the gas flow paths 61, 64, 65, and 67 to 69, an air supply device such as a compressor, a pressure reducing valve, a measuring instrument such as a pressure gauge, and the like can be appropriately installed. In addition, in the liquid flow paths 62 and 63, a liquid supply device such as a pump, a measuring instrument such as a flow meter, and the like can be appropriately installed.

The recovery device 1 is a device that recovers carbon dioxide.

A gas G1 containing carbon dioxide such as air and an exhaust gas is supplied to the concentration unit 11. In the concentration unit 11, carbon dioxide of the gas G1 is concentrated. As the concentration unit 11, a known concentration device can be used as long as it can concentrate carbon dioxide, and for example, a membrane separation device using a difference in permeation rate with respect to the membrane or an adsorption separation device using chemical or physical adsorption and desorption can be used. Particularly, as the concentration unit 11, a chemical adsorption and particularly a temperature swing adsorption unit is preferable because it has excellent separation performance.

A concentrated gas G2 in which carbon dioxide is concentrated in the concentration unit 11 is sent to the absorption unit 12 via the gas flow path 61. In addition, a separated gas G3 separated from the concentrated gas G2 is sent to the gas-liquid separator 42 via the gas flow path 69.

In the absorption unit 12, carbon dioxide gas in the concentrated gas G2 supplied from the concentration unit 11 comes into contact with an absorption liquid A1, and carbon dioxide is dissolved in the absorption liquid A1 and absorbed. A method of bringing carbon dioxide gas into contact with the absorption liquid A1 is not particularly limited, and examples thereof include a method of performing bubbling by blowing the concentrated gas G2 into the absorption liquid A1, The absorption liquid A1 may be any liquid that can absorb carbon dioxide and discharge dioxide gas with heating, and examples thereof include ethanolamine.

An absorption liquid A2 in which carbon dioxide is absorbed in the absorption unit 12 is sent to the discharge unit 13 through the liquid flow path 62. In the discharge unit 13, the absorption liquid A2 is heated using heat generated in the reaction container 41 of the homologation reaction device 4 to be described below, and carbon dioxide gas G3 is discharged from the absorption liquid A2. As the discharge unit 13, for example, a known heat exchanger can be used.

The carbon dioxide gas G3 discharged from the discharge unit 13 is sent to the electrochemical reaction device 2 through the gas flow path 64.

Figure 2:
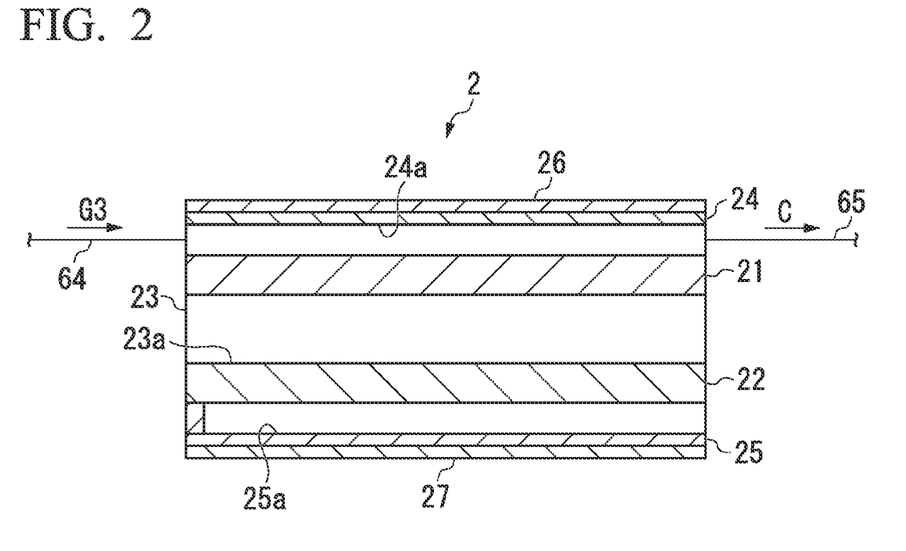
FIG. 2 is a cross-sectional view showing an example of an electrochemical reaction device in the carbon dioxide treatment device in FIG. 1.

The electrochemical reaction device 2 is a device that electrochemically reduces carbon dioxide. As shown in FIG. 2, the electrochemical reaction device 2 includes a cathode 21, an anode 22, a liquid flow path structure 23 that forms an electrolytic solution flow path 23a, a first gas flow path structure 24 that forms a cathode-side gas flow path 24a, a second gas flow path structure 25 that forms a gas discharge path 25a, a first feed conductor 26, and a second feed conductor 27.

In the electrochemical reaction device 2, the first feed conductor 26, the first gas flow path structure 24, the cathode 21, the liquid flow path structure 23, the anode 22, the second gas flow path structure 25, and the second feed conductor 27 are laminated in that order. A slit is formed in the liquid flow path structure 23, and a part of the slit surrounded by the cathode 21, the anode 22, and the liquid flow path structure 23 becomes the electrolytic solution flow path 23a. A groove is formed in the first gas flow path structure 24 on the side of the cathode 21, and a part of the groove surrounded by the first gas flow path structure 24 and the cathode 21 becomes the cathode-side gas flow path 24a. A groove is formed in the second gas flow path structure 25 on the side of the anode 22, and a part of the groove surrounded by the second gas flow path structure 25 and the anode 22 becomes the gas discharge path 25a.

In this manner, in the electrochemical reaction device 2, the electrolytic solution flow path 23a is formed between the cathode 21 and the anode 22, the cathode-side gas flow path 24a is formed on the side opposite to the anode 22 of the cathode 21, and the gas discharge path 25a is formed on the side opposite to the cathode 21 of the anode 22. The first feed conductor 26 and the second feed conductor 27 are electrically connected to the storage unit 32 of the power storage device 3. In addition, the first gas flow path structure 24 and the second gas flow path structure 25 are conductors, and a voltage can be applied between the cathode 21 and the anode 22 by power supplied from the storage unit 32.

The cathode 21 is an electrode that reduces carbon dioxide and reduces water. The cathode 21 may be any electrode as long as it can electrochemically reduce carbon dioxide and the generated gaseous product permeates to the cathode-side gas flow path 24a, and an electrode in which a cathode catalyst layer is formed on a gas diffusion layer on the side of the electrolytic solution flow path 23a is an exemplary example. A part of the cathode catalyst layer may enter the gas diffusion layer. A porous layer that is denser than the gas diffusion layer may be arranged between the gas diffusion layer and the cathode catalyst layer.

As the cathode catalyst that forms the cathode catalyst layer, a known catalyst that promotes reduction of carbon dioxide can be used. Specific examples of cathode catalysts include metals such as gold, silver, copper, platinum, palladium, nickel, cobalt, iron, manganese, titanium, cadmium, zinc, indium, gallium, lead, and tin, alloys thereof, intermetallic compounds, and metal complexes such as a ruthenium complex and a rhenium complex. Among these, copper and silver are preferable, and copper is more preferable because reduction of carbon dioxide is promoted. One of the cathode catalysts may be used alone or two or more thereof may be used in combination.

As the cathode catalyst, a supported catalyst in which metal particles are supported on a carbon material (carbon particles, carbon nanotubes, graphene, etc.) may be used.

The gas diffusion layer of the cathode 21 is not particularly limited, and examples thereof include carbon paper and carbon cloth.

A method of producing the cathode 21 is not particularly limited, and a method in which a liquid composition containing a cathode catalyst is applied to a surface of the gas diffusion layer on the side of the electrolytic solution flow path 23a and dried is an exemplary example.

The anode 22 is an electrode that oxidizes hydroxide ions to generate oxygen. The anode 22 may be any electrode as long as it can electrochemically oxidize hydroxide ions and the generated oxygen permeates to the gas discharge path 25a, and an electrode in which an anode catalyst layer is formed on the gas diffusion layer on the side of the electrolytic solution flow path 23a is an exemplary example.

As the anode catalyst that forms the anode catalyst layer is not particularly limited, and a known anode catalyst can be used. Specific examples thereof include metals such as platinum, palladium, and nickel, alloys thereof, intermetallic compounds, metal oxides such as manganese oxide, iridium oxide, nickel oxide, cobalt oxide, iron oxide, tin oxide, indium oxide, ruthenium oxide, lithium oxide, and lanthanum oxide, and metal complexes such as a ruthenium complex and a rhenium complex. One of these anode catalysts may be used alone or two or more thereof may be used in combination.

As the gas diffusion layer of the anode 22, for example, carbon paper and carbon cloth are exemplary examples. In addition, as the gas diffusion layer, a porous product such as a mesh material, a punching material, a porous component, and a metal fiber sintered product may be used. Examples of materials of porous products include metals such as titanium, nickel, and iron, and alloys thereof (for example, SUS).

Examples of materials of the liquid flow path structure 23 include a fluororesin such as polytetrafluoroethylene.

Examples of materials of the first gas flow path structure 24 and the second gas flow path structure 25 include metals such as titanium and SUS, and carbon.

Examples of materials of the first feed conductor 26 and the second feed conductor 27 include metals such as titanium and SUS, and carbon. As the first feed conductor 26 and the second feed conductor 27, a conductor obtained by performing a plating treatment such as gold plating on a surface of a copper substrate may be used.

In the electrochemical reaction device 2, an electrolytic solution B flows through the electrolytic solution flow path 23a. The electrolytic solution flowing out from the outlet of the electrolytic solution flow path 23a is returned to the inlet of the electrolytic solution flow path 23a through a circulation flow path 66 provided outside the electrochemical reaction device 2 and circulates.

Examples of electrolytic solutions B include a potassium hydroxide aqueous solution and a sodium hydroxide aqueous solution. Among these, the potassium hydroxide aqueous solution is preferable because it has excellent solubility of carbon dioxide in the absorption unit 12 and reduction of carbon dioxide in the electrochemical reaction device 2 is promoted.

The carbon dioxide gas G3 supplied from the discharge unit 13 flows through the cathode-side gas flow path 24a. Then, when a voltage is applied to the cathode 21 and the anode 22, carbon dioxide is electrochemically reduced in the following reaction in the cathode 21, and carbon monoxide and ethylene are generated. In addition, hydrogen is generated by water electrolysis caused by carbon dioxide reduction. A gaseous product C containing ethylene and hydrogen generated in the cathode 21 passes through the gas diffusion layer of the cathode 21, flows out from the cathode-side gas flow path 24a, and is sent to the reaction container 41 through the gas flow path 65.

$$CO_2+H_2O \rightarrow CO+2OH^-$$

$$2CO+8H_2O \rightarrow C_2H_4+8OH^-+2H_2O$$

$$2H_2O \rightarrow H_2+2OH^-$$

In addition, hydroxide ions generated in the cathode 21 move in the electrolytic solution B to the anode 22, and are oxidized in the following reaction to generate oxygen. Oxygen generated in the anode 22 passes through the gas diffusion layer of the anode 22 and is discharged from the gas discharge path 25a.

$$4OH^- \rightarrow O_2+2H_2O$$

The power storage device 3 is a device that supplies power to the electrochemical reaction device 2.

In the conversion unit 31, renewable energy is converted into electrical energy. The conversion unit 31 is not particularly limited, and examples thereof include a wind power generator, a solar power generator, and a geothermal power generator. The number of conversion units 31 included in the power storage device 3 may be one or two or more.

In the storage unit 32, the electrical energy converted by the conversion unit 31 is stored. When the converted electrical energy is stored in the storage unit 32, power can be stably supplied to the electrochemical reaction device 2 during a time period in which the conversion unit does not generate power. In addition, when renewable energy is used, generally, voltage fluctuations tend to be large, but when energy is temporarily stored in the storage unit 32, power can be supplied to the electrochemical reaction device 2 at a stable voltage.

The storage unit 32 may be any unit in which charging and discharging can be performed, and examples thereof include a nickel hydride battery and a lithium ion secondary battery. Among these, the nickel hydride battery is preferable because an electrolytic solution can be communized and shared using potassium hydroxide as an electrolyte.

The homologation reaction device 4 is a device that increases the number of carbons by multimerizing ethylene generated when carbon dioxide is reduced in the electrochemical reaction device 2.

The gaseous product C containing ethylene generated in the cathode 21 of the electrochemical reaction device 2 is sent to the reaction container 41 through the gas flow path 65. In the reaction container 41, a multimerization reaction of ethylene is performed in the presence of an olefin multimerization catalyst. Accordingly, for example, an olefin having an extended carbon chain such as 1-butene, 1-hexene, and 1-octene can be produced.

The olefin multimerization catalyst is not particularly limited, and a known catalyst used in the multimerization reaction can be used, and examples thereof include a solid acid catalyst using silica alumina or zeolite as a carrier, and a transition metal complex compound.

In the homologation reaction device 4 of this example, a generated gas D after the multimerization reaction flowing out from the reaction container 41 is sent to the gas-liquid separator 42 through the gas flow path 67. An olefin having 6 or more carbon atoms is liquid at room temperature. Therefore, for example, when an olefin having 6 or more carbon atoms is a desired carbon compound, if the temperature of the gas-liquid separator 42 is set to about 30° C., an olefin having 6 or more carbon atoms (an olefin liquid E1) and an olefin having less than 6 carbon atoms (an olefin gas E2) can be easily gas-liquid separated. In addition, if the temperature of the gas-liquid separator 42 is raised, the number of carbon atoms of the obtained olefin liquid E1 can be increased.

When the gas G1 supplied to the concentration unit 11 of the recovery device 1 is air, a separated gas G4 sent from the concentration unit 11 through the gas flow path 69 may be used to cool a generated gas K in the gas-liquid separator 42. For example, using the gas-liquid separator 42 including a cooling pipe, a separated gas G4 is passed through the cooling pipe, and a generated gas D is passed outside the cooling pipe and aggregated on the surface of the cooling pipe to form an olefin liquid E1. In addition, the olefin gas E2 separated by the gas-liquid separator 42 contains an unreacted component such as ethylene and an olefin having a smaller number of carbon atoms than a desired olefin, it can be returned to the reaction container 41 through the gas flow path 68, and re-used in the multimerization reaction.

The multimerization reaction of ethylene in the reaction container 41 is an exothermic reaction in which a supply material has a higher enthalpy than a product material, and the reaction enthalpy is negative. In the carbon dioxide treatment device 100, reaction heat generated in the reaction container 41 of the homologation reaction device 4 is used to heat the absorption liquid A2. Accordingly, since it is not necessary to prepare a new heat source device for discharging the carbon dioxide gas G3 from the absorption liquid A2, the energy efficiency is improved.

The homologation reaction device 4 may further include a reaction container in which a hydrogenation reaction of an olefin obtained by multimerizing ethylene is performed using hydrogen generated in the electrochemical reaction device 2, or a reaction container in which an isomerization reaction of olefin and paraffin is performed.

(Method of Producing Carbon Compound)

A method of producing a carbon compound of the present embodiment includes the following processes (a) to (c).

Process (a): carbon dioxide is recovered.

Process (b): the recovered carbon dioxide is electrochemically reduced to obtain ethylene.

Process (c): Ethylene generated when carbon dioxide is reduced is multimerized.

In the process (a), first, an exhaust gas, air or the like is supplied as the gas G1 to the concentration unit 11, and carbon dioxide is concentrated to obtain a concentrated gas G2. The carbon dioxide concentration of the concentrated gas G2 can be appropriately set, and can be, for example, 25 to 85 vol %.

Next, the concentrated gas G2 is supplied from the concentration unit 11 to the absorption unit 12, the concentrated gas G2 is brought into contact with the absorption liquid A1, and carbon dioxide in the concentrated gas G2 is dissolved in the absorption liquid A1 and absorbed. The absorption liquid A2 that has absorbed carbon dioxide is sent to the discharge unit 13, the absorption liquid A2 is heated using reaction heat of the reaction container 41, and the carbon dioxide gas G3 is discharged. The discharged carbon dioxide gas G3 is supplied to the electrochemical reaction device 2.

In the process (b), the electrolytic solution B flows through the electrolytic solution flow path 23*a* of the electrochemical reaction device 2, the carbon dioxide gas G3 flows through the cathode-side gas flow path 24*a*, power is supplied from the power storage device 3 to the electrochemical reaction device 2, and a voltage is applied between the cathode 21 and the anode 22. Then, carbon dioxide is electrochemically reduced in the cathode 21, and a gaseous product C containing ethylene and hydrogen is generated. The gaseous product C passes through the gas diffusion layer of the cathode 21 and flows out from the cathode-side gas flow path 24*a*. In addition, in the anode 22, hydroxide ions in the electrolytic solution B are oxidized to generate oxygen. Oxygen passes through the gas diffusion layer of the anode 22, and is discharged from the gas discharge path 25*a*.

In the process (c), the gaseous product C containing ethylene generated in the cathode 21 of the electrochemical reaction device 2 is sent to the reaction container 41, and brought into gas-phase contact with the olefin multimerization catalyst in the reaction container 41, and ethylene is multimerized. Accordingly, an olefin in which ethylene is multimerized is obtained. For example, when an olefin having 6 or more carbon atoms is used as a desired carbon compound, the generated gas D discharged from the reaction container 41 is sent to the gas-liquid separator 42, and cooled to about 30° C. Then, since a desired olefin having 6 or more carbon atoms (for example, 1-hexene) is liquefied, and an olefin having less than 6 carbon atoms remains as a gas, they can be easily separated as the olefin liquid E1 and the olefin gas E2. The number of carbon atoms of the olefin liquid E1 and the olefin gas E2 to be gas-liquid separated can be adjusted through the temperature of gas-liquid separation.

The olefin gas E2 after gas-liquid separation can be returned to the reaction container 41, and reused in the multilayer reaction. In this manner, when an olefin having a smaller number of carbon atoms than a desired olefin is circulated between the reaction container 41 and the gas-liquid separator 42, in the reaction container 41, it is preferable to adjust a time for which a raw material gas (a mixed gas containing the gaseous product C and the olefin gas E2) is in contact with a catalyst, and control conditions in which each olefin molecule causes an average of one multilayer reaction. Accordingly, since an unintentional increase of the number of carbon atoms of the olefin generated in the reaction container 41 is prevented, an olefin having a desired number of carbon atoms (the olefin liquid E1) can be selectively separated in the gas-liquid separator 42.

According to such a method, valuable substances can be efficiently obtained from a renewable carbon source with high selectivity. Therefore, it does not require a large-scale purifying facility such as a distillation column required in the conventional petrochemistry using a Fischer-Tropsch (FT) synthesis method or an MtG method and is comprehensively economically advantageous.

The reaction temperature of the multimerization reaction is preferably 200 to 350° C.

The reaction time of the multimerization reaction, that is, the time for which a raw material gas is in contact with an olefin multimerization catalyst, is preferably 10 to 250 g·min./mol in W/F because an excessive multimerization reaction is minimized and the selectivity of a desired carbon compound is improved.

As described above, in a first embodiment, an absorption liquid is heated using reaction heat of an ethylene multimerization reaction in the homologation reaction device, and carbon dioxide gas recovered by absorbing it into the absorption liquid is discharged and electrically reduced. Therefore, energy efficiency for recovering and reducing carbon dioxide is high.

Second Embodiment (Carbon Dioxide Treatment Device)

Figure 3:
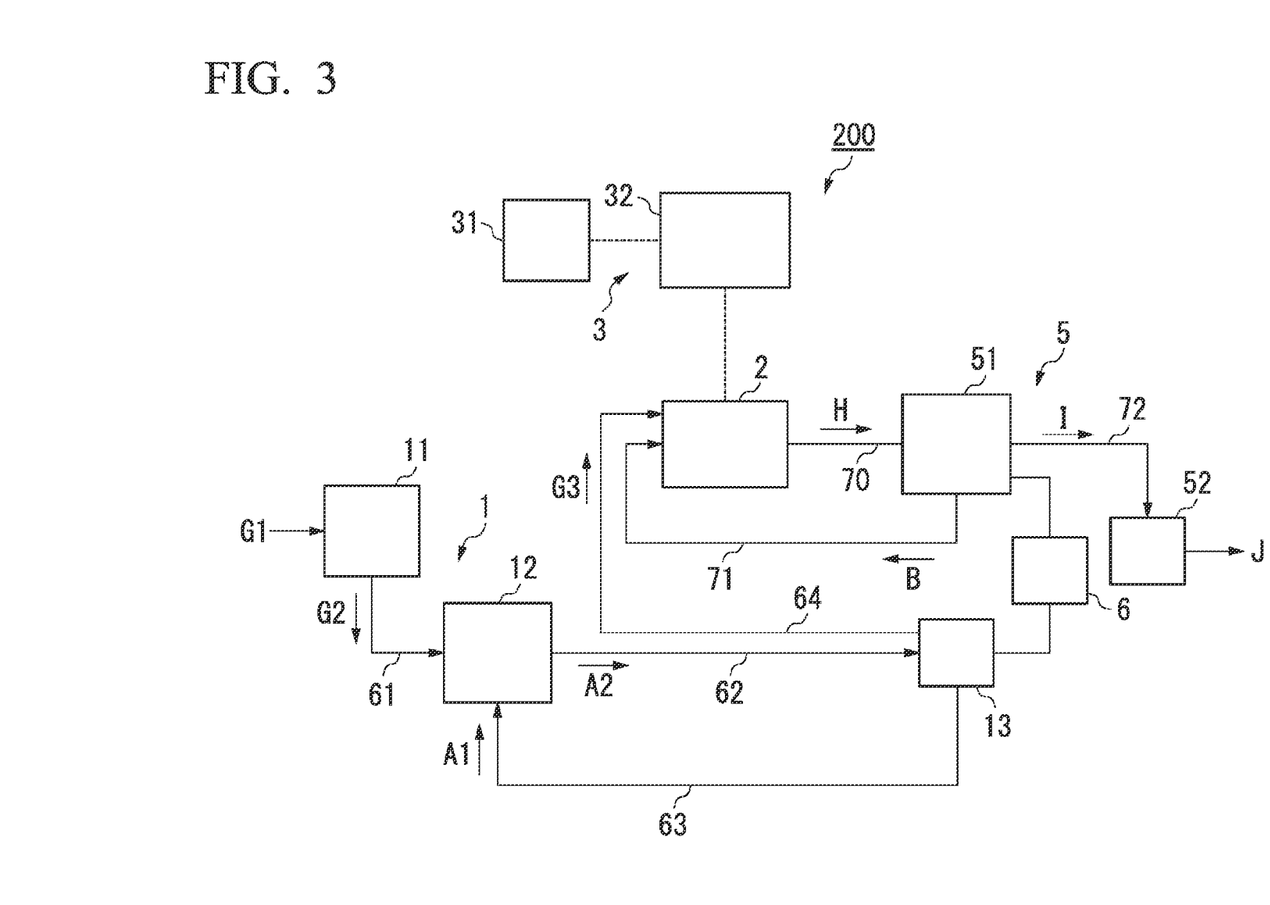
FIG. 3 is a block diagram showing a carbon dioxide treatment device of a second embodiment.

A carbon dioxide treatment device may include an ethanol purifying device that purifies ethanol generated when carbon dioxide is reduced in an electrochemical reaction device. Specifically, for example, a carbon dioxide treatment device 200, an exemplary example of which is shown in FIG. 3, may be used. Parts in FIG. 3 that are the same as those in FIG. 1 will be denoted with the same reference numerals and descriptions thereof will be omitted.

The carbon dioxide treatment device 200 includes an ethanol purifying device 5 in place of the homologation reaction device 4 in the carbon dioxide treatment device 100.

The ethanol purifying device 5 includes a distillation column 51 and a gas-liquid separator 52. The distillation column 51 is connected to the outlet of the electrolytic solution flow path 23a of the electrochemical reaction device 2 via a liquid flow path 70. The distillation column 51 and the gas-liquid separator 52 are connected via a gas flow path 72. The distillation column 51 and the inlet of the electrolytic solution flow path 23a of the electrochemical reaction device 2 are connected via a liquid flow path 71.

In the carbon dioxide treatment device 200, since ethanol generated when carbon dioxide is reduced in the cathode 21 is obtained as a liquid mixture H with the electrolytic solution B, the liquid mixture H is sent to the distillation column 51 through the liquid flow path 70 and distilled. An ethanol gas I separated by distillation is sent to the gas-liquid separator 52 through the gas flow path 72, and recovered as a liquid ethanol J. The electrolytic solution B from which ethanol is separated in the distillation column 51 is sent to the electrolytic solution flow path 23a of the electrochemical reaction device 2 through the liquid flow path 71 and circulated.

The carbon dioxide treatment device 200 further includes a heat source device 6 that supplies heat to the discharge unit 13 of the recovery device 1 and the distillation column 51 of the ethanol purifying device 5. In this manner, in the carbon dioxide treatment device 200, the heat source device 6 is shared by the discharge unit 13 and the distillation column 51. Therefore, the energy efficiency is higher compared with when a heat source device is separately prepared for the discharge unit 13 and the distillation column 51.

The heat source device 6 is not particularly limited, and examples thereof include an exhaust heat recovery device in a factory and the like.

(Method of Producing Carbon Compound)

A method of producing a carbon compound using the carbon dioxide treatment device 200 includes the following process (d) in place of the process (c).

Process (d): ethanol generated when carbon dioxide is reduced is purified.

In the method of producing a carbon compound using the carbon dioxide treatment device 200, like the method using the carbon dioxide treatment device 100, carbon dioxide is absorbed into the absorption liquid A1 and recovered, the absorption liquid A2 that has absorbed carbon dioxide is heated in the discharge unit 13, and carbon dioxide gas G2 is discharged. Then, the carbon dioxide gas G2 is supplied to the electrochemical reaction device 2, and carbon dioxide is electrochemically reduced. Ethanol generated when carbon dioxide is reduced is obtained as the liquid mixture H with the electrolytic solution B. Therefore, after the liquid mixture H is distilled in the distillation column 51 of the ethanol purifying device 5, gas-liquid separation is performed to purify the ethanol. The heat sent from the heat source device 6 is used to heat the absorption liquid A2 in the discharge unit 13 and heat the liquid mixture H in the distillation column 51. In this manner, it is possible to produce ethanol using the carbon dioxide treatment device 200.

As described above, in a second embodiment, an absorption liquid is heated using reaction heat of an ethylene multimerization reaction in the homologation reaction device, and carbon dioxide gas recovered by absorbing it into the absorption liquid is discharged and electrically reduced. Therefore, energy efficiency for recovering and reducing carbon dioxide is high.

In addition, the carbon dioxide treatment device including an ethanol purifying device may be a carbon dioxide treatment device further including the ethanol purifying device 5 in addition to the homologation reaction device 4.

In addition, components in the embodiments can be appropriately replaced with well-known components without departing from the spirit of the present invention, and the above-modified examples may be appropriately combined.

While preferred embodiments of the invention have been described and illustrated above, it should be understood that these are exemplary examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

EXPLANATION OF REFERENCES 100, 200 Carbon dioxide treatment device
1 Recovery device
2 Electrochemical reaction device
3 Power storage device
4 Homologation reaction device
5 Ethanol purifying device
11 Concentration unit
12 Absorption unit
13 Discharge unit
21 Cathode
22 Anode
23a Electrolytic solution flow path
24a Cathode-side gas flow path
31 Conversion unit
32 Storage unit
41 Reaction container
42 Gas-liquid separator
51 Distillation column
52 Gas-liquid separator
A1, A2 Absorption liquid
B Electrolytic solution

What is claimed is:

1. A carbon dioxide treatment device, comprising
a recovery device that recovers carbon dioxide;
an electrochemical reaction device that electrochemically reduces carbon dioxide recovered by the recovery device; and
a homologation reaction device that increases the number of carbons by multimerizing ethylene generated when carbon dioxide is reduced in the electrochemical reaction device,
wherein the recovery device includes an absorption unit that brings carbon dioxide gas into contact with an absorption liquid and absorbs carbon dioxide into the absorption liquid, and a discharge unit that heats the absorption liquid that has absorbed carbon dioxide and discharges carbon dioxide gas, and
wherein the discharge unit heats the absorption liquid using heat generated in a multimerization reaction of the homologation reaction device.

2. The carbon dioxide treatment device according to claim 1, further comprising
a power storage device that supplies power to the electrochemical reaction device,
wherein the power storage device includes a conversion unit that converts renewable energy into electrical energy, and a storage unit that stores electrical energy converted by the conversion unit.

3. A method of producing a carbon compound using the carbon dioxide treatment device according to claim 1, comprising
a process of recovering carbon dioxide;
a process of electrochemically reducing the recovered carbon dioxide to obtain ethylene; and
a process of multimerizing ethylene generated when carbon dioxide is reduced.

4. The carbon dioxide treatment device according to claim 1, wherein the carbon dioxide treatment device further comprises a gas flow path, which sends carbon dioxide gas which is heated using heat generated in the homologation reaction device and discharged from the discharge unit, to the electrochemical reaction device.

* * * * *